United States Patent

Ho

[11] Patent Number: 5,910,992
[45] Date of Patent: Jun. 8, 1999

[54] STETHOSCOPE WITH AN INDEXING DETENT

[76] Inventor: Chi-Sheng Ho, No. 65, Cheng Tien Rd., Tu Cheng, Taipei Hsien, Taiwan

[21] Appl. No.: 09/009,875

[22] Filed: Jan. 21, 1998

[51] Int. Cl.[6] ....................................................... A61B 7/04
[52] U.S. Cl. ............................................. 381/67; 181/131
[58] Field of Search .............................. 381/67; 181/131; 600/528, 523

[56] References Cited

U.S. PATENT DOCUMENTS

| | | | |
|---|---|---|---|
| 3,303,903 | 2/1967 | Speelman | 181/131 |
| 4,723,555 | 2/1988 | Shue | 381/67 |
| 4,770,270 | 9/1988 | Grimm | 181/131 |
| 5,737,429 | 4/1998 | Lee | 381/67 |
| 5,774,563 | 6/1998 | DesLauriers et al. | 381/67 |

Primary Examiner—Ping Lee
Attorney, Agent, or Firm—Bacon & Thomas, PLLC

[57] ABSTRACT

A stethoscope with an indexing detent comprises a hollow body, a rotary tubular shaft, a and an indexing detent. The hollow body comprises two different microphones and a plurality of openings with the same diameters as that of the microphones. The rotary tubular shaft can be rotated around the hollow body, and it further comprises an axial hole whose central axis is aligned with that of the rotary tubular shaft, and a plurality of circular through holes at the locations related to the openings. On one of the circular through holes, there is a lock ball. Inside the rotary tubular shaft, there exist a resilient element which pushes the lock ball outward. When the circular through holes are directly aligned with the openings, the lock ball is pushed outward by the compressible resilient element and then partially goes into one opening to lock the related locations of the rotary tubular shaft and the hollow body. Meanwhile, the lock ball also airtightly shuts one circular through hole, hence there forms a passageway between the axial hole and another opening.

4 Claims, 3 Drawing Sheets

STETHOSCOPE WITH AN INDEXING DETENT

FIELD OF THE INVENTION

The present invention relates to a stethoscope with an indexing detent, specially an airtight, easily made, and simple stethoscope which just induces smallest friction force and little abrasion when exchange the microphones. Furthermore, the life time of the present invention is longer than the prior art.

BACKGROUND OF THE INVENTION

Stethoscopes is an important device to detect the tones of the acoustic wave from the client's body, hence complaints of a client can be diagnosed by doctors in auscultation.

As shown in FIG. 1, the conventional stethoscope is composed of a body with two microphones, a hollow shaft which can be rotated around the body and connected with the ear pipes to transfer the sound from the client's body (the ear pipes are not shown in the FIG. 1). There is a opening in each microphone to recess the acoustic wave and transfer it to the body. In the hollow shaft, there are through holes whose sizes matches with that of the openings. The through holes and the inner part of the hollow shaft form a passageway for the recessed acoustic wave travelling into the inner part of the hollow shaft when the hollow shaft rotates around the body and the through holes are directly aligned with the openings. In order to fix the related positions of the body and the hollow shaft, there are a ball and a pressed spring inside the hollow shaft and a curved groove inside the body. When the ball is directly aligned with the curved groove, the pressed spring pushes the ball outward to clamp the body and the hollow shaft.

It is important that, when the ball clamps the related locations of the body and the hollow shaft, the opening and the through hole must be exactly aligned. Otherwise, the through holes and the inner part of the hollow shaft will not form a passageway, and the recessed acoustic wave can not travel into the inner part of the hollow shaft. For the above-mentioned reason, a substantially high precision is needed in the fabrication of the conventional stethoscopes, which additionally increases the cost.

According to the U.S. Pat. No. 4,770,270, which discloses an indexing detent which is composed of a hollow cylindrical element with a beveled-shape seat end and a pressed spring. When the hollow cylindrical element is aligned with the opening of the body, the pressed spring pushes the hollow cylindrical element outward to clamp the body and the hollow shaft. The sound from the microphone then travels through the inner space of the hollow cylindrical element and into the hollow shaft. Hence, the positioning and acoustic connecting functions are immediately achieved. The beveled-shape seat end of the hollow cylindrical element however induces a large friction force when the hollow shaft is rotated around the body, this stethoscope will not work smoothly and will easily induce large abrasion.

BRIEF SUMMARY OF THE INVENTION

According to the above drawbacks of the prior arts, it is the major objective of the present invention to support a airtight, easily made, and simple stethoscope with an indexing detent, which generates the smallest friction force and works smoothly with the little abrasion.

DETAILED DESCRIPTION OF THE PREFERRED EMBODIMENT

Figure 1:
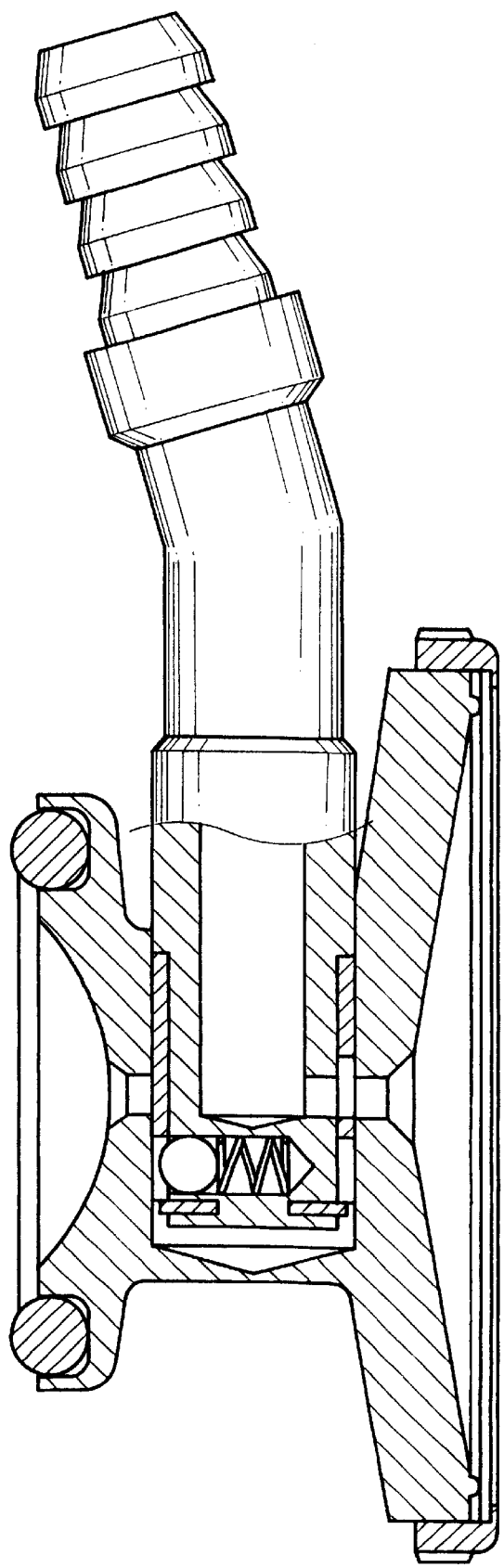
FIG. 1 is the cross-sectional view of the stethoscope according to the prior art.
Figure 2:
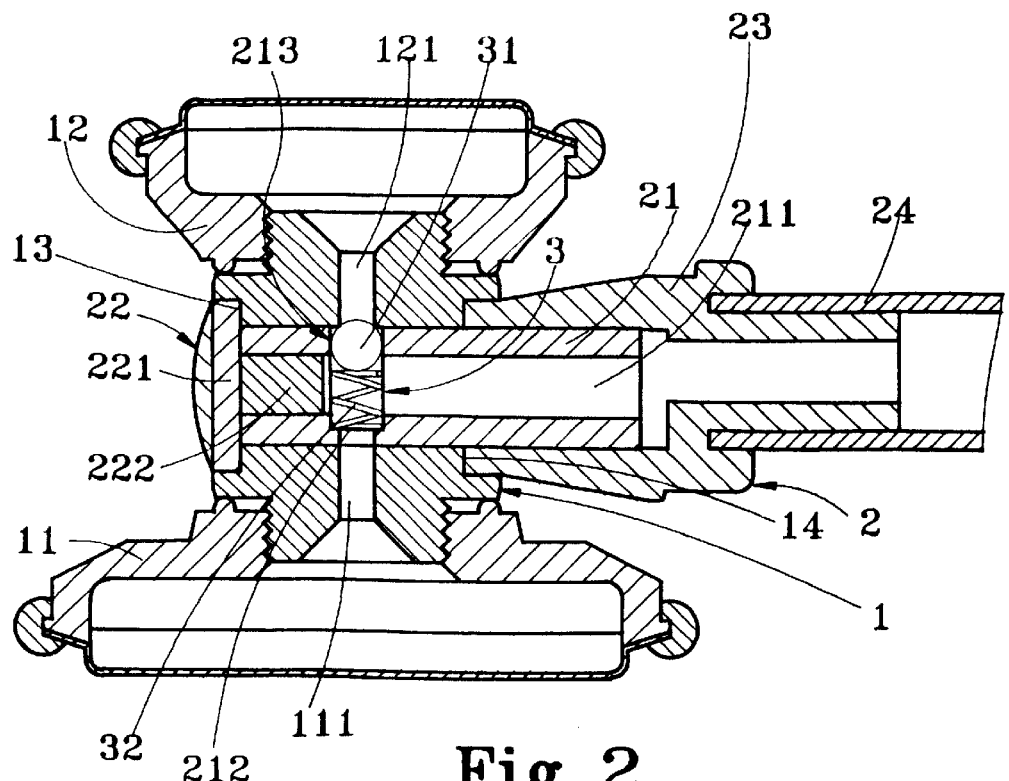
FIG. 2 is the cross-sectional view of the stethoscope according to the present invention.

Please refer to the FIG. 2. The present invention relates to a stethoscope with a positioning structure comprising a hollow body 1, a rotary tubular shaft 2 which is fixed inside the hollow body 1 with a related rotational axis, and an indexing detent 3.

There are two bell type microphones 11 and 12 on both sides of the hollow body 1. On both microphones, there exist two openings 111 and 121 independently with the same diameters as that of the microphones 11 and 12. Since the microphones 11 and 12 are related to the prior art, the detailed description is skipped.

The rotary tubular shaft 2 comprises an axial hollow tube 21, a covering hat 22 and a cylindrical hollow connecting seat 23 on both ends of the axial hollow tube 21. On one end of the hollow connecting seat 23, there is an ear pipe 24 made of some soft and resilient materials. Inside the axial hollow tube 21, there is an axial hole 211 which is completely 10 connected to the openings 111 and 121, and the size of the axial hole 211 is larger than both sizes of the circular through holes 212 and 213 between the openings 111 and 121. Therefore, the induced acoustic wave from the microphones 11 and 12 is then transferred into the axial hole 211. The above-mentioned covering hat 22 further comprises a head 221 whose outer diameter is larger than that of the axial hollow tube 21, and a plug rod 222 which can be plugged into and exactly match with the axial hole 211. The head 221 is limited by the left flange 13 of the hollow body 1, thus the plug rod 222 can rigidly and airtightly shut the left opening of the axial hole 211. The inside wall of the hollow connecting seat 23 airtightly matches with the outside wall of the axial hollow tube 21, and the left end of the hollow connecting seat 23 is limited by the right flange 14 of the hollow body 1. Hence, the axial hollow tube 21 is clamped and its location is rigidly fixed inside the hollow body 1.

The indexing detent 3 further comprises a lock ball 31 inside the circular through hole 212 (or 213), and a resilient element 32 inside the axial hollow tube 21 (such as a conventional coil-shaped and compressible spring). The resilient element 32 always pushes the lock ball 31 outward under the normal condition.

From detailed description of the present invention according to the above paragraphs, the axial hollow tube 21 can be rotated around the hollow body 1, and the circular through holes 212, 213, and the openings 111, 121 are consequently connected to form a passageway for the acoustic waves passing therethrough.

Figure 3A:
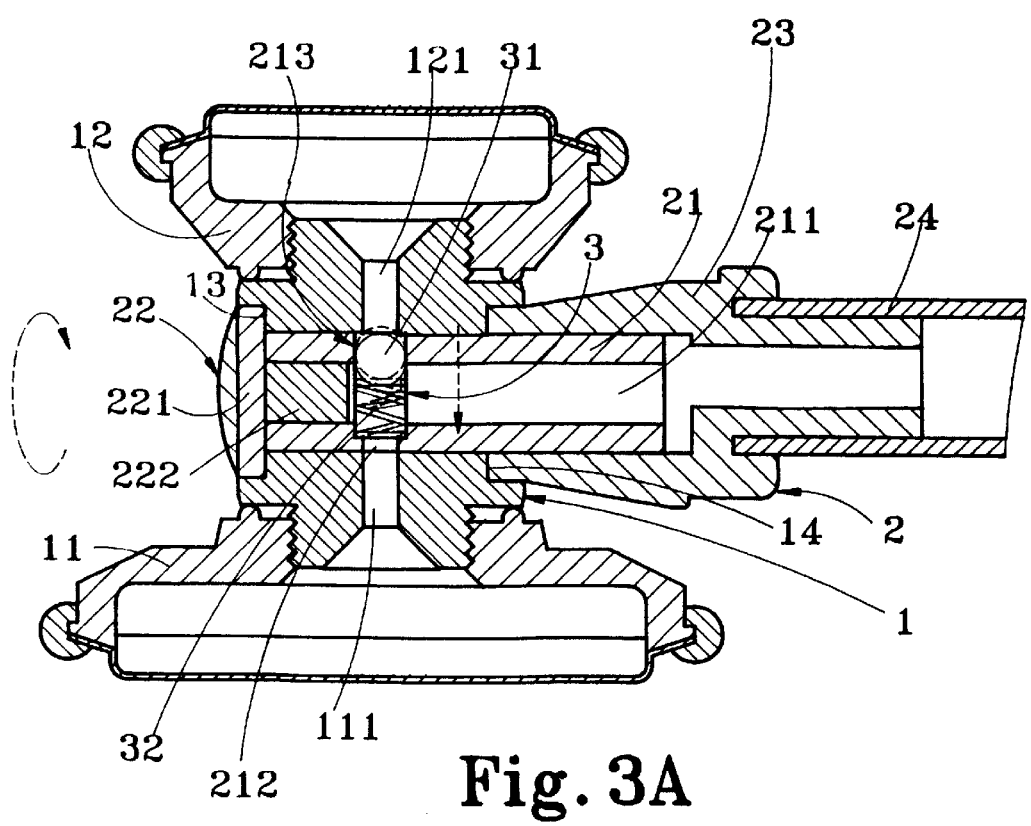
FIG. 3A is the schematic drawing of the present invention during operation.
Figure 3B:
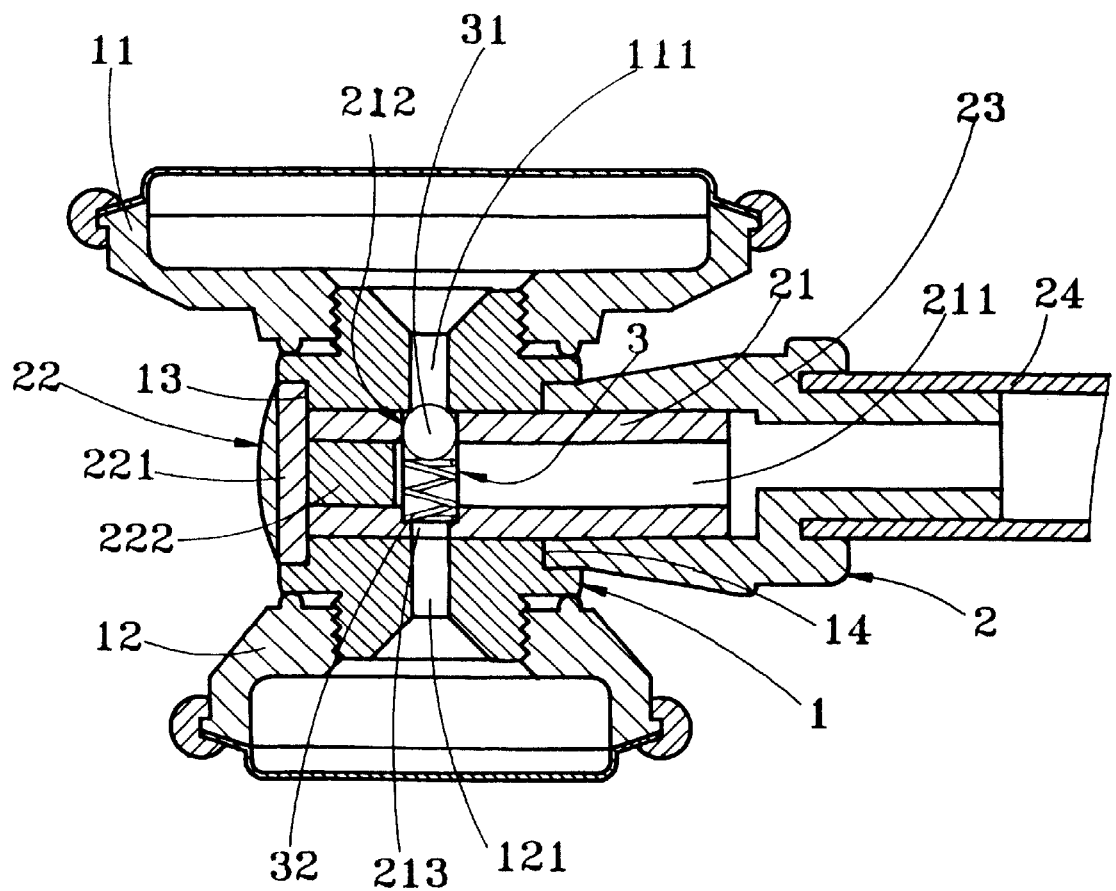
FIG. 3B is the second schematic drawing of the present invention during operation.

Please refer to FIG. 3A and FIG. 3B. These drawings describe the operation of the stethoscope according to the present invention. When the rotary tubular shaft 2 rotates around the hollow body 1 and the circular through holes 212 and 213 are not directly aligned with the openings 111 and 121, the lock ball 31 is indeed contacted to the inside wall of the hollow body 1, and the resilient element 32 is compressed by the lock ball 31 (as shown in FIG. 3A). When the rotary tubular shaft 2 still rotates around the hollow body 1 and the circular through holes 212 and 213 are directly aligned with the openings 111 and 121, the lock ball 31 is pushed outward by the compressible resilient element 32 and then partially goes into the opening 111 to lock the related locations of the rotary tubular shaft 2 and the hollow body 1 (as shown in FIG. 3B). At the same time, the lock ball 31 also airtightly shuts the circular through hole 212, hence there forms a passageway between the axial hole 211 and another opening 121.

From the above description, the indexing detent 3 of the present invention supports a positioning function of the hollow body 1 and the rotary tubular shaft 2. The structure of the indexing detent 3 according to the present invention is less complicated than the prior art, and its fabrication is also easier. In addition, since the lock ball 31 used for positioning in the indexing detent 3 is round, the induced friction force is smallest when the rotary tubular shaft 2 rotates around the hollow body 1. It is smooth and easy to exchange the microphones 11 and 12 with little abrasion. Furthermore, the life time of the indexing detent 3 according to the present invention is longer than the prior art.

To sum up, the structure of the indexing detent used for the stethoscopes of the present invention is innovative and practically feasible. The indexing detent of stethoscopes described above is the preferred embodiment of the present invention for the purposes of illustration only, and is not intended as a definition of the limits and scope of the invention disclosed. Any modifications and variations that may be apparent to a person skilled in the art are intended to be included within the scope of the present invention.

What is claimed is:

1. A stethoscope with an indexing detent comprising a hollow body, a rotary tubular shaft which is clamped inside and can rotate around said hollow body, and an indexing detent, wherein said hollow body comprises a plurality of microphones for receiving acoustic waves of different frequencies, and a plurality of openings with the same diameters as the microphones;

said rotary tubular shaft comprises an axial hole whose central axis is aligned with that of said rotary tubular shaft, and a plurality of circular through holes at the locations directly and respectively coupled to said openings concurrently when said rotary shaft is turned to a position, wherein the central axes of said circular through holes are aligned with the diameter of said axial hole, and their diameters are larger than that of said openings for the induced acoustic wave from said microphone travelling through said circular through holes into said axial hole; and said indexing detent comprises a lock ball inside one of said circular through holes, and a resilient element inside said rotary tubular shaft, wherein the resilient element pushes said lock ball outward.

2. The stethoscope with an indexing detent of claim 1, wherein said rotary tubular shaft further comprises a hollow tube with said axial hole and said circular through holes thereon, a covering hat, and a hollow connecting seat, wherein said covering hat and hollow connecting seat are independently set on both ends of said hollow tube, and are used for rigidly fixing said rotary tubular shaft to said hollow body.

3. The stethoscope with an indexing detent of claim 2, wherein said covering hat further comprises a plug rod that can be airtightly plugged into said axial hole.

4. The stethoscope with an indexing detent of claim 1, wherein said resilient element is a coil-shaped and pressed spring.

* * * * *